(12) United States Patent
Atilio Los

(10) Patent No.: US 10,786,458 B2
(45) Date of Patent: Sep. 29, 2020

(54) PROCEDURE FOR PREPARING ENTERIC-COATED PELLETS CONTAINING A PROTON PUMP INHIBITOR AND MULTI-PARTICLE PHARMACEUTICAL COMPOSITIONS CONTAINING THEM

(71) Applicants: LABORATORIOS BAGO S.A., Buenos Aires (AR); Eastbrand Holding GMBH, Vienna (AT)

(72) Inventor: Mario Atilio Los, Buenos Aires (AR)

(73) Assignees: Laboratorios Bago S.A., Buenos Aires (AR); Eastbrand Holding GMBH, Vienna (AT)

(*) Notice: Subject to any disclaimer, the term of this patent is extended or adjusted under 35 U.S.C. 154(b) by 28 days.

(21) Appl. No.: 15/563,181

(22) PCT Filed: Mar. 31, 2015

(86) PCT No.: PCT/EP2015/056982
§ 371 (c)(1),
(2) Date: Sep. 29, 2017

(87) PCT Pub. No.: WO2016/155786
PCT Pub. Date: Oct. 6, 2016

(65) Prior Publication Data
US 2018/0078505 A1    Mar. 22, 2018

(51) Int. Cl.
| | |
|---|---|
| A61K 9/16 | (2006.01) |
| A61K 31/4439 | (2006.01) |
| A61K 31/196 | (2006.01) |
| A61K 9/00 | (2006.01) |
| A61K 9/50 | (2006.01) |
| A61K 9/20 | (2006.01) |
| A61K 9/48 | (2006.01) |
| A61K 31/4184 | (2006.01) |

(52) U.S. Cl.
CPC ......... *A61K 9/1676* (2013.01); *A61K 9/0056* (2013.01); *A61K 9/0095* (2013.01); *A61K 9/1611* (2013.01); *A61K 9/1617* (2013.01); *A61K 9/1635* (2013.01); *A61K 9/1652* (2013.01); *A61K 9/1682* (2013.01); *A61K 9/2077* (2013.01); *A61K 9/2081* (2013.01); *A61K 9/4808* (2013.01); *A61K 9/5078* (2013.01); *A61K 9/5084* (2013.01); *A61K 9/5089* (2013.01); *A61K 31/196* (2013.01); *A61K 31/4184* (2013.01); *A61K 31/4439* (2013.01)

(58) Field of Classification Search
CPC . A61K 9/1676; A61K 9/1682; A61K 31/4184
See application file for complete search history.

(56) References Cited

U.S. PATENT DOCUMENTS

| | | | |
|---|---|---|---|
| 6,228,400 B1* | 5/2001 | Lee | A61K 9/5078 424/451 |
| 2007/0141151 A1* | 6/2007 | Silver | A61K 9/0056 424/472 |
| 2009/0028941 A1* | 1/2009 | Cowles | A61K 9/0065 424/469 |
| 2012/0058194 A1 | 3/2012 | Vaya et al. | |

FOREIGN PATENT DOCUMENTS

| | | |
|---|---|---|
| DE | 102008045339 A1 | 3/2010 |
| EP | 1018340 A1 * | 7/2000 |
| WO | WO-2004062552 A2 | 7/2004 |
| WO | WO2-005004921 A * | 1/2005 |
| WO | WO-2006134611 A1 | 12/2006 |

OTHER PUBLICATIONS

PCT/EP2015/056982 International Search Report, dated Sep. 22, 2015.

* cited by examiner

*Primary Examiner* — Lakshmi S Channavajjala
(74) *Attorney, Agent, or Firm* — Julie K. Staple; Dinsmore & Shohl LLP

(57) ABSTRACT

Procedure for preparing enteric-coated pellets containing a proton pump inhibitor with benzimidazole structure, useful for preparing multi-particle pharmaceutical compositions for oral use that comprises the following stages: I) coat pure cellulose cores with a hydroalcoholic suspension that contains the proton pump inhibitor, a dibasic amino acid and polyvinylpyrrolidone; II) isolate the coated pure cellulose cores obtained in Stage I; III) apply an enteric coating to the particles obtained in Stage II above; and IV) dry the particles obtained in Stage III above and separate by size.

11 Claims, No Drawings

PROCEDURE FOR PREPARING ENTERIC-COATED PELLETS CONTAINING A PROTON PUMP INHIBITOR AND MULTI-PARTICLE PHARMACEUTICAL COMPOSITIONS CONTAINING THEM

REFERENCE TO RELATED APPLICATION

This application is the U.S. National Stage under 35 U.S.C. § 371 of PCT Patent Application No. PCT/EP2015/056982, filed Mar. 31, 2015, the entire content of which is incorporated herein by reference.

This invention relates to a procedure for preparing enteric-coated pellets comprising pure cellulose cores containing on the surface thereof a substantially uniform distribution of a proton pump inhibitor with benzimidazole structure together with a dibasic amino acid as the internal protection agent mainly in an amorphous state, preferably completely amorphous, a recrystallisation inhibitor of the dibasic amino acid and subsequent enteric coating; wherein the contents of the proton pump inhibitor is more than 10.5% and preferably more than 12.0% and the average pellet size is less than 710 microns, preferably between 350 and 500 microns.

The invention also relates to the multi-particle pharmaceutical compositions either in the form of oral disintegration tablets, powder for suspension or capsules comprising the pellets obtained by the process of the invention.

The multi-particle pharmaceutical compositions of the invention have the advantage that they are not contraindicated in patients who have "lactose intolerance" or diabetic patients.

The pellets are useful for preparing multi-particle pharmaceutical compositions characterized because they are easy to take and particularly easy to administer to patients who have difficulty swallowing even when their feeding is normal.

BACKGROUND OF THE INVENTION

Oral tablets are the preferred pharmaceutical format and use in human medicine.

The preparation of oral tablets has several associated practical problems which, since the invention of the first tablet during the 1890s, have required searching for specific technological solutions applicable to each case and to each particular problem.

So, for example, in the respective technologies developed, subjects of special interest, inter alia, have been, (a) facilitating preparation, (b) masking the taste of the active ingredient they contain (c) ensuring the stability of the active ingredient vis-à-vis excipients in the tablets and even vis-à-vis the acid medium in the stomach, (d) increase the bioavailability of the active ingredient, and others, improving the overall quality of the tablets produced.

In the last two decades some developed technologies have focused on facilitating tablet swallowing, others on improving the absorption of the active ingredient they contain and others on incorporating both advantages.

One of the drawbacks observed during the use of tablets in human medicine is the frequent difficulty in taking them, mainly in children and old-aged patients. The difficulty in taking them is a consequence of problems with swallowing due to different causes (psychic or physical), a particularly significant difficulty in patients with dysphagia caused by certain pathologies like Parkinson's disease, neurological problems or nauseous states.

The difficulty in swallowing also exists among adults who usually have no drawbacks with their normal feeding. thus, it is highlighted, inter alia, as follows:
a study on a national scale in USA (USA TODAY—The Society for the Advancement of Education—Oct. 2004) describes that:
a) more than 40% of the adult population has problems in swallowing tablets, even when they have no difficulty swallowing food or drink,
b) that swallowing problems cause: a delay in taking the medicine (14%), missing the dose (8%) or abandoning the treatment (4%).
Another study in Norway (Anderson o et al (1995)—Tidsskr, Nor Laegerforen—115, 947-949) carried out on 6158 general medicine patients revealed that approximately 26% of these patients did not take the medication prescribed because of problems associated with swallowing. The problems were linked to the size of the tablet, its surface or taste.

As is well known, the basis of the success or failure of the therapeutic treatment depends on the continuity of the treatment indicated to the patient.

In the last decade an alternative for overcoming the drawbacks mentioned was the increasing development of orodispersable type tablets known by the FDA under the acronym ODT (Oral Disintegration Tablets).

Such tablets have various advantages:
1) They are easy to administer to adult patients and particularly, to geriatric patients and children.
2) They are particularly useful for administering to patients who are non-cooperative, disabled, have mental problems or dysphagia conditions.
3) They do not need to be taken with water.
4) In contact with the saliva they disintegrate immediately forming an easy-to-swallow suspension.
5) They offer the possibility of pre-gastric absorption (mouth, pharynx, oesophagus) partially or completely avoiding the first hepatic step and improving the bioavailability of the active ingredient.
6) They improve adherence to the treatment.

The preparation of this type of oral disintegration tablets is more complex than the preparation of the traditional oral tablets because of the significant number of technical problems that must be resolved. This is revealed by the numerous technologies patented or mentioned in the technical bibliography. So, for example, Amit Kumar et al., J. Pharm. Educ. Res., Vol. 2, Issue No 1, June 2011; Fernandez Tabares D. F. et al., Ars. Pharm., 2009, Vol. 50 No. 3, 153-167; and others.

Another alternative has been the preparation of compositions in the form of powder for suspension or small size capsules. Both are feasible only when the nature of the active ingredient allows it.

Another objective of increasing technological interest, mainly during the last two decades has been, and is, to improve the bioavailability of the active ingredient.

An interesting alternative that helps to improve drug bioavailability are the multi-particle pharmaceutical formats (Multiple Unit Dose) which unlike the traditional pharmaceutical forms (or Single Unit Dose) are made up of a significant number of small particles (granules, pellets) containing the pharmaceutically active ingredient.

The multi-particle pharmaceutical compositions are presented as tablets or capsules and they are characterised by releasing after intake a significant number of particles that are distributed uniformly over the gastrointestinal tract. They have the advantage over traditional forms of avoiding the concentration of the whole drug contained in the composition, simultaneously in one part of the gastrointestinal tract, minimising the risk of local toxicity.

Generally multi-particle compositions have the following advantages:

1) More uniform distribution of the active ingredient they contain through the gastrointestinal tract.

2) Eating has less of an effect on the absorption of the active ingredient

3) The release of the active ingredient in the composition can be repeated.

4) Statistically there is less variability of absorption between patients or in the same patient with different administering.

5) Vis-à-vis active ingredients with low solubility they offer the possibility of greater absorption linked to a better distribution of the active ingredient in the gastrointestinal tract.

6) Greater probability of a total release of the active ingredient in the pharmaceutical composition and consequently, greater absorption and bioavailability.

The technical literature is extensive in describing the advantages of the multi-particle systems over the mono-particle or single unit dose.

Also the EMEA (The European Medicines Agency—London, Jul. 29, 1999—Regulation CPMP/QWP/604/96) has generally declared itself in favour of multi-particle compositions:

"The development of single non-disintegrating dosage forms is discouraged since their residence time in the stomach is unpredictable and in general longer than disintegrating dosage forms with multiple units or pellets."

Solid multi-particle pharmaceutical preparations are mentioned frequently in the technical literature. Thus, for example:

Document U.S. Pat. No. 5,464,632 describes a multi-particle tablet with a suitable disintegration speed in contact with the saliva in the buccal cavity.

Document GB A 2.147.501 mentions an oral disintegration tablet that contains paracetamol in the presence of hydroxypropyl cellulose and ethyl cellulose.

Document U.S. Pat. No. 5,026,560 mentions spherical particles that have a core coated with the active ingredient and hydroxypropyl cellulose, but the tablets do not disintegrate orally.

Document JP-A-5-271054 describes the preparation of tablets that dissolve rapidly and comprise sugars as well as the active ingredient.

However, in the previous documents aimed at oral disintegration tablets, none of the parts describe the presence of an active ingredient that is unstable vis-à-vis the acidity in the stomach and consequently, neither do they teach how to technically resolve the preparation of multi-particle pharmaceutical compositions containing drugs that are unstable in an acid medium.

Among the active ingredients sensitive to the gastric acid medium because of their distinctive instability, proton pump inhibitors are focused, like omeprazole, lanzoprazole, pantoprazole, esomeprazole or rabeprazole. All of them are very unstable vis-à-vis stomach acid pH. Almost in a few minutes they are completely destroyed. Also, such inhibitors are used according to the patient's need in compositions comprising between 10 and 80 milligrams per unit dose.

The instability in an acid medium and the wide dose range mentioned above determine the need to have a flexible technology for preparing the chosen multi-particle pharmaceutical composition.

Documents U.S. Pat. No. 7,431,942 (Oct. 7, 2008) and ES 2.274.625 T3 (May 16, 2007) specifically describe an oral disintegration table made up of:

1) Fine granules with an average particle diameter of 400 microns.

2) The granules are made up of a neutral core containing crystalline cellulose (40 to 50% by weight) and 50% or more lactose.

3) The cellulose and lactose cores are coated with a benzimidazole compound (specifically, lanzoprazole) which is sensitive to the acids in the gastric medium. Specifically, lanzoprazole, which is insoluble in water, is added in a solid state, forming an aqueous suspension over the cellulose and lactose cores.

4) These cores are coated with a basic inorganic salt.
The basic inorganic salt described in all the examples is magnesium carbonate in a crystalline physical state.
The inorganic salt is present in more than 30% of the weight of the active benzimidazole compound to contribute to the stability of the benzimidazole compound in an acid medium.

5) The cores subsequently comprise a first stage of aqueous enteric coating (methacrylate copolymer) and a subsequent layer made up of a sugar alcohol (erythritol or mannitol).

The presence of lactose in the cores mentioned is significant, approximately 50% of the weight thereof.

In association with lactose the literature indicates that, it is not advisable to administer it to patients who have "lactose intolerance", a complex pathology caused by the reduction or absence of the lactose enzyme in the intestinal microvilli. This absence or reduction of lactose determines the impossibility of metabolising lactose and causing among other things: poor absorption, weight loss, undernourishment or abdominal cramps.

The authors also describe other basic inorganic salts of sodium, potassium or calcium with a particularly preferable content of approximately 20 to 50% by weight with respect to the benzimidazole compound contained by the pellets or particles.

The neutral core coating mentioned above is carried out by spraying with a liquid that contains the benzimidazole compound, the basic inorganic salt and hydroxypropyl cellulose in water; organic solvent or a mixture of organic solvent and water is not used.

The oral disintegration tablets prepared with the previous cores and known excipients of pharmaceutical use have a disintegration time of one minute or less.

Also European Patent Application EP 1.813.275 A1 describes the preparation of buccal disintegration tablets.

These oral disintegration tablets comprise one or more particles or sub-tablets with enteric coating that contain the acid-sensitive drug and which comprise:

1) The neutral core made up specifically of sucrose, as table sugar is called technically, which is usually contraindicated in patients with diabetes.

It does not contain an alkaline stabilising agent and it is coated directly with a benzimidazole type drug (lanzoprazole) which is acid-sensitive.

2) A first coating that is applied also without an alkaline stabiliser.

3) Subsequently, an inorganic type alkaline stabiliser is applied.

The alkaline stabiliser is inorganic and comprises calcium or magnesium carbonate or a mixture of both.

The magnesium carbonate content is more than 50% of the contents by weight of lanzoprazole contained in the enteric-coated particles (so, for example, Table I indicates: lanzoprazole 30 mg and magnesium carbonate 15 mg).

4) Over the alkaline protection an enteric coating of methacrylic acid copolymer is applied.

5) And by mixing the particles or sub-tablets with an enteric coating containing one or more excipients the oral disintegration tablets are obtained.

6) Finally, according to Table 2 (page 9 of patent EP 1 813 275 A1) the tablets are prepared with 50% by weight of two optionally chosen excipients that contain lactose, they are:

a) STARLAC (made up of 85% of lactose monohydrate and 15% cornstarch)

Specifically tablets of 708 mg contain 378.5 mg of STARLAC, others of 750 mg contain 394 mg and tablets of 592 mg contain 322 mg of STARLAC, virtually, about 300 mg of lactose per tablet.

b) CELLACTOSE 80 (made up of 75% monohydrate lactose and 25% cellulose)

Specifically, tablets with an end weight of 526 mg, have 234 mg of CELLACTOSE 80 and tablets with an end weight of 560 mg contain 249 mg of CELLACTOSE 80, also with a high lactose content.

Administering tablets with a high lactose content is not advisable for patients who need lanzoprazole, but who specifically have "lactose intolerance" because of the known problems caused in these patients when they take lactose because of the absence of the lactose enzyme in the intestinal villi.

Both Patents Describe Respectively:

a) The use of lactose and cellulose cores in different percentages preparing tablets with a high lactose content b) The use of sugar or sucrose cores.

c) They suffer from the drawback that the intake of lactose is contraindicated in patients with "lactose intolerance" and the intake of sugar is contraindicated in patients with diabetes.

d) Both limit themselves to using an inorganic alkaline stabilising agent, in solid state and with a high content. This contributes to the larger average size of the pellets they make.

However, neither of the documents contain the teachings or unexpected technical advantages of using pure cellulose cores, as described in this invention.

Therefore there is still the need to provide small size tablets that contain active ingredients which are labile in the acid medium in the stomach, and with sufficient stability to release the active ingredient early in the intestinal pH where the ingredient is absorbed, and which allow the preparation of multi-particle pharmaceutical compositions that are easy to take irrespective of whether they are in the form of oral disintegration tablets, powder for suspension or capsules, and which can be administered also to patients with diabetes or with lactose intolerance.

SUMMARY OF THE INVENTION

Therefore a first object of the invention is to provide pellets that comprise a proton pump inhibitor with convenient stability in the gastric acid medium for preparing multi-particle pharmaceutical compositions for oral use.

Another object of the invention is to provide new pure cellulose pellets that contain the active ingredient with benzoimidazole structure and with inhibiting activity on the proton pump that are useful for preparing a pharmaceutical composition which, after intake, do not degrade at pH 4.5 for 45 minutes and have the capacity to release said inhibitor at pH 6.8.

Another object of the invention is to provide new pure cellulose pellets that contain the active ingredient with benzoimidazole structure distributed over the cellulose cores.

Another object of the invention is to provide small size enteric-coated pellets of a proton pump inhibitor allowing the preparation of oral disintegration multi-particle pharmaceutical compositions, powder for suspension or capsules smaller than those commercially available.

Another object of the invention is to provide enteric-coated pellets that comprise a proton pump inhibitor with sufficient technological flexibility for them to be applied to the preparation of different pharmaceutical compositions that are needed in each case and which according to the characteristics of the pellets in a different average diameter range, withstand the compression stage during the preparation of the multi-particle pharmaceutical compositions in the form of oral disintegration tablets with the characteristic advantages thereof.

Another object of the invention is to provide small size enteric-coated pellets but which comprise a proton pump inhibitor and have a high content thereof thereby ensuring the necessary intake for the patient's treatment.

Another object of the invention is to provide pharmaceutical compositions that are presented in the multi-particle form with the biopharmaceutical advantages broadly described for these compositions, and with the ability to facilitate their intake by the patient and spread the dosage.

Another object of this invention is to provide pharmaceutical compositions that are presented in the multi-particle form, which can be administered to patients with both diabetes and lactose intolerance.

DETAILED DESCRIPTION OF THE INVENTION

This invention relates to a new procedure for preparing particles or pellets comprising pure cellulose cores containing on the surface thereof an even distribution of a proton pump inhibitor with benzimidazole structure together with a dibasic amino acid as the internal protection agent mainly in amorphous form, preferably completely amorphous, a recrystallisation inhibitor of the dibasic amino acid (preferably polyvinylpyrrolidone and very preferably polyvinylpyrrolidone K 30) and an enteric coating as the external coating agent which together determine the chemical stability of the active ingredient vis-à-vis the acid medium in the stomach in the chosen pharmaceutical composition containing said pellets.

The pure cellulose cores have the advantage of being inert, the cellulose is not hydrolysed in the body and it is not contraindicated in patients with diabetes or with "glucose intolerance".

The cellulose is formed by the union of beta-1,4 glucopyranose molecules that form beta-1,4 glucosidic bonds which when hydrolysed produce glucose. But, in human beings and animals due to the lack of the cellulase enzyme they do not produce glucose; consequently the pure cellulose cores are inert.

The literature also highlights that it is important to include cellulose in the human diet as a dietary fibre to facilitate digestion.

The previous art does not describe the coating of pure cellulose cores with a hydroalcoholic suspension that contains previously dissolved, a proton pump inhibitor with benzimidazole structure and a dibasic amino acid in a mixture of ethanol and water (preferably between 80:20 and 95:5) which subsequently is transformed into a suspension when talcum is added together with the cohesion or binding agent (polyvinylpyrrolidone) which acts by inhibiting the recrystallization of the dibasic amino acid.

The new above solution of the proton pump inhibitor with benzimidazole structure in ethanol-water (preferably between 80:20 and 95:5) determines the even distribution of the proton pump inhibitor with benzimidazole structure over all the pure cellulose cores, with said previous dissolution preventing the greater concentration of the proton pump inhibitor with benzimidazole structure over part of the total mass and ensures an uniform distribution of all the particles.

Neither do the state of the art documents describe the new use of organic agents as alkaline stabilisers (dibasic amino acids) with advantages not described under the inorganic stabilisers mentioned in the literature.

The dibasic amino acid used as the internal protector in this invention is dissolved previously together with the proton pump inhibitor and, this way, through subsequent elimination of the solvent containing them, an even distribution of the dibasic amino acid and the active ingredient is obtained over the surface of the cores, with both components (dibasic amino acids and active ingredient) moving into a solid state. Unexpectedly, this way sufficient internal protection is offered to the active ingredient unstable in the acid medium.

The notable protection of the dibasic amino acid is effective with only about 10.0% by weight with respect to the weight of the active ingredient. This advantage is not described previously in the technical literature.

Whereas, with the inorganic agents mentioned in the previous art, which are in the solid state, a simple physical mixture is formed with the proton pump inhibitor agent and therefore it is necessary to use a high percentage (30 to 50%) of said inorganic agents to ensure the stability of the proton pump inhibitor agent.

These new characteristics, together with the small average size of the enteric-coated pellets (smaller than 710 microns and preferably smaller than 500 microns) and the stability in the acid medium of the active ingredient they contain, enable them to transform subsequently into new chosen pharmaceutical compositions.

This invention provides a new procedure for preparing pellets with sufficient technological flexibility to apply them to the preparation of different pharmaceutical compositions that are needed in each case and according to their characteristics as pellets in a different average diameter range.

The chosen oral compositions are presented in the form of oral disintegration tablets (ODT), powder for suspension in water or other liquids, capsules (preferably smaller than those commercially available) or multi-particle tablets.

They all contribute to the easy intake by patients and have multi-particle properties.

They contain the proton pump inhibitor with benzoimidazole structure and excellent protection against the acid pH in the stomach and it is possible to obtain them as described in this invention in the experimental part, using dibasic amino acids in mainly amorphous state and pure cellulose cores.

The active ingredient with benzoimidazole structure and proton pump inhibitor activity contained in the pharmaceutical composition in the form of new pure cellulose pellets, after intake, does not degrade at pH 4.5 for 45 minutes and has the capacity to release said inhibitor at pH 6.8 in no more than 45 minutes according to the assay described in British Pharmacopea (BP) 2012 Vol. III.

The instability of omeprazole in the acid medium is widely known and described in the technical literature and in the literature on patents.

It is also known that a simple enteric coating using some of the usual procedures described in the technical literature for other active ingredients, is not sufficient for preparing omeprazole pharmaceutical compositions with convenient stability in the gastric acid medium.

A practical problem that this invention has resolved and which is also applicable to other proton pump inhibitors with benzimidazole structure like esomeprazole, lanzoprazole, pantoprazole or rabeprazole.

The compositions of this invention are presented in the multi-particle form with the biopharmaceutical advantages broadly described for these compositions, with the capacity to facilitate intake thereof by the patient and spread the dose.

The chosen composition of this invention is presented preferably in the form of oral disintegration tablets (ODT).

The oral disintegration tablets (ODT) can be administered directly. But, they have the characteristic of being able to be poured over water or another drink and after their complete disintegration, which takes less than a minute and preferably less than 30 seconds, they can be administered as a suspension to adult patients with swallowing problems or paediatric patients also. In both cases, according to the volume of suspension administered, it is possible to regulate the dose. The ODT tablets described also offer convenient dose flexibility.

The small size of the enteric-coated pellets containing the proton pump inhibitor with benzimidazole structure in this invention and the possibility of selection through sieving during the preparation thereof also enable preparing capsules smaller than those commercially available. The commercially available pellets containing the proton pump inhibitor with benzimidazole structure or those described in the literature have an average particle size range of about 1000 microns. A size significantly larger than those in this invention. Consequently, the capsules containing them are a larger size.

The small capsules described in the examples in the experimental part maintain the multi-particle nature and facilitate intake thereof by patients with swallowing problems. They have the following practical applications:

a) due to being smaller than other capsules they contribute to administering to patients with swallowing problems (even when they have no problems with normal eating).

b) it is possible to pour the contents of the capsule into water or another liquid and administer the suspension gradually in spoonfuls.

c) in hospitalised patients who have a nasogastric tube in place, via this route it is possible to administer a suspension made up of the small pellets from the capsules and water.

The preparation of enteric-coated pellets containing the proton pump inhibitor with benzimidazole structure according to this invention is carried out over neutral pure cellulose cores.

The pure cellulose cores as mentioned, have the advantage of being inert, since the cellulose does not hydrolyse in the intestine because of the lack of the cellulase enzyme and it does not produce glucose in human beings. Consequently they can be applied to patients with diabetes and also it is known that in the human diet the presence of cellulose in the intestine facilitates digestion.

To date no description has been given of the use of neutral pure cellulose cores for preparing pellets coated with proton pump inhibitors.

Neither has a description been given of the use of such pellets in a new association of the proton pump inhibitor with benzimidazole structure and a protective agent of the dibasic amino acid type. As will be explained, and particularly useful and necessary for preparing a composition that is stable in an acid medium.

A description has only been given, as mentioned in the background to the invention, of: A) cores made up of cellulose and lactose, and B) others made up of sugar both used as a support for lanzoprazole, and not suitable for applying to patients with "lactose intolerance" or diabetes.

Commercially pure cellulose cores exist with a broad particle size range. These include: cores with a particle size range between 106 and 212 microns, between 150 and 300 microns, between 300 and 500 microns, between 500 and 710 microns and others of a larger size. Some are sold under the Celphere Brand and they are prepared by the Company Asahi Kasei.

These pure cellulose cores, as will be seen, are of special practical interest for the present invention to allow for the preparation of pellets with a different average diameter range and, what is very important, with a high active ingredient content. Both aspects are particularly interesting for preparing the chosen pharmaceutical composition.

Using an organic internal protection agent of the dibasic amino acid type during the preparation of the pellets, surprisingly allows an even coating of the proton pump inhibitor with benzimidazole structure over the cellulose cores. In principle the internal protection agent is dissolved in the medium and finally, together with a binding agent that inhibits the recrystallisation of the amino acid when the solvent is removed, the amino acid is deposited over the particles mainly (and even completely) in an amorphous physical state.

The intimate or internal protection agent of the proton pump inhibitor with benzimidazole structure is a dibasic amino acid, preferably selected from among lysine, histidine or 1-arginine, with 1-arginine being the most preferred one.

The prior dissolution of the internal protection agent of the dibasic amino acid in water and of the proton pump inhibitor with benzimidazole structure in the water-ethanol mixture in the presence of the binding agent (polyvinylpyrrolidone) determines that the internal protection agent is mainly (or even completely) in an amorphous state when the solvent is eliminated and it is distributed evenly together with the proton pump inhibitor with benzimidazole structure over the cellulose cores, ensuring intimate or internal protection vis-à-vis acids and humidity.

Surprisingly, the practical importance of the previous dissolution of the dibasic amino acid in the presence of the binding agent (polyvinylpyrrolidone) was observed under a microscope and it is the object of special practical interest for this invention. The polyvinylpyrrolidone known as a binding agent acts simultaneously as a crystallisation inhibitor during the evaporation over the cellulose cores of the solvents mixture (water-ethanol) and determines:

a) Even distribution of the dibasic amino acid and of the proton pump inhibitor with benzimidazole structure over the surface of the pure cellulose cores.

b) Presence of the dibasic amino acid in an amorphous state.

c) In the physical amorphous state, the dibasic amino acid offers a greater contact surface with the acid medium, and consequently, it has an unexpected neutralising capacity d) Only the presence of about 10% of the dibasic amino acid by weight is necessary with respect to the weight of the proton pump inhibitor with benzimidazole structure (on the surface of the pure cellulose cores) to ensure protection of the active ingredient from the acidity.

The contents of only about 10% of the dibasic organic agent constitutes a significant difference with the basic protective but inorganic agents that exist in a physical crystalline state and which are mentioned and described previously in the background art.

The basic inorganic agents must exist in high contents to ensure the stability in the acid medium of the active ingredient.

Thus it is mentioned, for example, in U.S. Pat. No. 7,431,942 where the magnesium carbonate exists as between and 40% of the weight of the benzimidazole compound and in EP 1.813.275 where the contents is more than 50%.

The smaller necessary content using a dibasic amino acid also determines the small size of the pellets obtained, and allows for the preparation of the different chosen pharmaceutical compositions of this invention.

Surprisingly, it has been observed experimentally that the binding agent (polyvinylpyrrolidone) prevents the recrystallisation of the dibasic amino acid, preferably lysine, histidine or 1-arginine, and very preferably 1-arginine, dissolved in a mixture made up of water-ethanol (between 20:80 and 5:95) after the evaporation of the solvent, and it determines the even distribution of the dibasic amino acid and the active ingredient over all the particles.

The drying of the pellets to humidity lower than 1%, surprisingly showed that it is particularly useful, since with time it determines the greater stability of the proton pump inhibitor with benzimidazole structure they contain, in the acid medium and vis-à-vis humidity.

Surprisingly it has been achieved that the pellets obtained by the procedure described in the examples have a high content of proton pump inhibitor with benzimidazole, more than 10.5%, preferably more than 12.0%.

The high content of the proton pump inhibitor with benzimidazole structure in the pellets prepared with the procedure described allows for the preparation of multi-particle pharmaceutical compositions, that are easy to take and surprisingly useful for patients with swallowing difficulties.

The procedure for preparing the enteric particles that contain the proton pump inhibitor with benzimidazole structure, which is the object of this invention, includes four continuous stages. Each stage fulfils a specific function and the whole determines the stability in the acid medium that the multi-particle pharmaceutical composition needs.

Preferably, the procedure, as illustrated in the preparation examples, comprises diagrammatically:

Stage I: The object is to provide pure cellulose cores coated evenly with the proton pump inhibitor, a dibasic amino acid, as protection agent, previously dissolved in an alcoholic solution, to finally end up in an amorphous state (or, at least, mainly amorphous), the agent inhibiting the recrystallisation of the internal protection and talcum.

The pure cellulose particles chosen for this invention have preferably an average diameter range between 150 and 300 microns. For example: Celphere type CP-203 or the like.

According to the chosen pharmaceutical composition other pure cellulose cores are also useful with different average particle diameter ranges than the one above (for example: 106 to 212 microns, Celphere type CP-102), 300 to 500 microns (Celphere CP-305).

The incorporated talcum has preferably a particle size average diameter of about 74 microns (#200 mesh).

Once prepared and dried the cellulose cores with the proton pump inhibitor in the benzimidazole structure in the indicated form contain:

1) The dibasic amino acid in amorphous form uniformly distributed together with the proton pump inhibitor with the benzimidazole structure over the cellulose cores, produces internal protection to the acid medium, and 2) Talcum, which due to its capacity to absorb humidity also contributes to the stability of the proton pump inhibitor.

Stage II: The object is to isolate through spray coating the particles obtained in Stage I.

Isolation that is carried out preferably with hydroxypropyl methylcellulose previously suspended in isopropyl alcohol-water, together with other components (polyethylene glycol 400, polysorbate 80 and titanium dioxide) as will be specified in the Examples.

The hydroxypropyl methylcellulose and other components intended to isolate the pure cellulose cores coated according to Stage I) and as described in the corresponding examples, can be replaced with commercially available mixtures that fulfil the same function, i.e.: act as isolating agents. So, for example, it is possible to use the commercial composition called Opadry White YS-1-7003 (hydroxypropyl methylcellulose, polyethylene glycol, polysorbate 80 and titanium dioxide).

Stage III: This corresponds to the enteric coating of the particles obtained in Stage II.

Surprisingly, it has been observed that the particles obtained in Stage II accept subsequently and indifferently an enteric coating using two different methods: a) hydroalcoholic and b) aqueous. In both cases such coating fulfils its specific function as described in the experimental part.

The two preferred coatings are:

Enteric Coating in Hydroalcoholic Medium.

The external protection agent is made up of Type A copolymer (USP/NF), triethyl citrate, glyceryl monostearate, polysorbate 80 and titanium dioxide and ethyl acrylate and methylmethacrylate copolymer dispersion (USP/NF).

In a non-limiting way a commercially available Type A copolymer is Eudragit L 100 and an ethyl acrylate and methylmethacrylate copolymer (USP/NF) is Eudragit NE 30 D.

Enteric Coating in Aqueous Medium.

Optionally, the external protection of the particles obtained in Stage II was also carried out in an exclusively aqueous medium containing methacrylic acid copolymer, triethyl citrate, glyceryl monostearate and polysorbate 80 as illustrated in the experimental part.

In this case also surprising was the high content of the proton pump inhibitor with benzimidazole structure in the enteric-coated pellets obtained, reaching 23%.

Such content has not been mentioned regarding enteric-coated pellets containing the proton pump inhibitor with the benzimidazole structure in the scope of the commercial supply of pellets containing the proton pump inhibitor with benzimidazole structure.

Neither in the technical literature to date are pellets with such a high content described.

The high content of the pellets obtained facilitates the subsequent preparation of the chosen pharmaceutical composition.

Stage IV: The object was to dry to humidity lower than 1% the pellets or particles obtained in Stage III and, preferably, select the particles by size range.

The dried enteric particles obtained in Stage III were sieved and the fraction of particles with an average size lower than 590 microns was selected for preparing the pharmaceutical composition.

Unexpectedly it was observed that the pellets with humidity more than 1% lost their initial stability to the acid medium and temperature more quickly.

Preferably, the coating suspension in Stage I) for coating the cellulose cores was prepared by:

i) dissolving the dibasic amino acid in water;

ii) adding ethanol to the previous solution (i) up to an ethanol-water proportion between 80:20 and 95:5 and preferably 90-10; and the proton pump inhibitor up to the complete dissolution thereof;

iii) adding talcum to the solution obtained in ii) to form a suspension, and subsequently adding polyvinylpyrrolidone (preferably polyvinylpyrrolidone K30) under stirring, preferably between 8500 and 10500 r.p.m, and very preferably at 9500 r.p.m.;

iv) filtering the suspension obtained in iii), preferably through a 250 micron mesh maintaining the suspension under stirring;

v) applying the previous suspension (iv) over pure cellulose cores, preferably with an average diameter of 150 to 300 microns, advantageously using a Wurster system (also called bottom spray), and preferably maintaining the temperature at 38 to 42° C. throughout the process; and vi) preferably sieving with a 500 micron mesh, to eliminate large size agglomerates.

The new enteric-coated pellets obtained according to the previous procedure and described in the experimental part have revealed:

a) That they have excellent stability vis-à-vis the proton pump inhibitor they contain in a pH 4.5 medium during 45 minutes and the capacity to release said inhibitor at pH 6.8 in no more than 45 minutes according to an assay described in British Pharmacopea 2012 Vol. III, as will be seen in the Experimental Part.

b) High content of proton pump inhibitor with benzimidazole structure in the enteric particles, not described previously, which is more than 10.5% and even more than 12.0%, according to the level of enteric coating (Stage II) chosen. With a content over 14% being especially preferable for the pharmaceutical composition.

c) That the procedure described is new because of the neutral pure cellulose cores and because of the presence of the organic internal protector (dibasic amino acid).

d) That the amino acid is present in an amount preferably less than or equal to 10% by weight with respect to the weight of the existent proton pump inhibitor with benzimidazole structure.

e) That it is applicable to neutral cores with different particle size ranges than the one mentioned above.

f) That the procedure offers the necessary and sufficient flexibility to prepare, according to the average diameter of the particles obtained in each case, the chosen multi-particle pharmaceutical composition.

This invention allows the chosen pharmaceutical composition prepared with the enteric particles to be presented (as described in the corresponding examples in the Experimental Part) indistinctively in the following formats:

a) Oral disintegration tablets.
b) Powder for suspension.
c) Capsules in a smaller size with an equal content of the active ingredient as other commercially available capsules to date, and which facilitate the intake thereof.
d) And in associations with microcapsules of sodium diclofenac prepared previously as described, inter alia, in international patent application WO 2013/139377 in the name of the same applicant of this invention. Preferably the prepared associations contain 25 to 100 mg of microencapsulated and enteric sodium diclofenac and between 10 and 40 mg of proton pump inhibitor with benzimidazole structure in pellets, and they are presented as oral disintegration tablets, powder for suspension or capsules.

In all cases new multi-particle and small size compositions can be prepared thanks to the fact that the pellets included have a high concentration of active ingredient.

In a non-limiting way, this invention will be described in greater detail in the following examples that describe the way of carrying it out practically.

Experimental Part

EXAMPLE I

Preparation of Enteric-Coated Pellets Containing Omeprazole

Starting with pure cellulose (100%) neutral cores and omeprazole pure active ingredient, with successive stages of bottom spray coating, using hydroalcoholic suspensions, enteric-coated omeprazole pellets were obtained, sized between 420 and 590 μm.

The preparation was carried out in four independent stages with each one fulfilling specific functions. They were:

Stage I: Coating Pure Cellulose Cores with a Hydroalcoholic Solution that Contains Dissolved Omeprazole and a Dibasic Amino Acid, and Forms the Suspension by Incorporating Talcum and Subsequently the Agent Polyvinylpyrrolidone.

The suspension presented the composition mentioned in Table I

TABLE 1

| Raw Material | Grams/100 g of suspension |
|---|---|
| Omeprazole | 14.7 |
| Polyvinylpyrrolidone K-30 | 3.6 |
| L-arginine | 1.5 |
| Talcum | 1.5 |
| Ethanol | 70.8 |
| Water | 7.9 |

The suspension was prepared by dissolving the 1-arginine in water; adding ethanol and dissolving omeprazole in the ethanol-water mixture formed. By adding the talcum it was transformed into a suspension that was homogeneised under stirring for 20 minutes. Subsequently, the polyvinylpyrrolidone K-30 was added, it was homogenised under stirring for another 20 minutes and the suspension was filtered through a 250 microns mesh.

Using bottom spray, a total of 15372 grams of this suspension, were applied to 2500 grams of pure cellulose cores sized between 150 and 300 μm, maintaining the temperature of the product between 38 and 42° C. throughout the process. At the end of this stage, a 500 μm sieve was used to eliminate agglomerates that could have formed during the process. Finally obtaining 5250 grams of omeprazole pellets protected by the dibasic amino acid.

Stage II: Isolating the Particles Obtained in Stage I

A hydroalcoholic suspension was prepared with hydroxypropyl methylcellulose (HPMC) and other components indicated in the formula in Table 2, under stirring for one hour.

TABLE 2

Composition of the isolating coating suspension.

| Raw Material | Grams/100 g of suspension |
|---|---|
| Hydroxypropyl methylcellulose (6 cp) | 3.66 |
| Hydroxypropyl methylcellulose (3 cp) | 3.66 |
| Polyethylene glycol 400 | 0.96 |
| Polysorbate 80 | 0.12 |
| Titanium Dioxide | 3.6 |
| Isopropyl Alcohol | 71 |
| Water | 17 |

A total of 2625 grams of the cores coated in Stage I were added to fluid bed equipment heated previously to 40° C. and they were coated using bottom spray with 7066 grams of the isolating suspension above. Throughout the process the temperature was maintained at 40 to 45° C. Using a 590 μm sieve agglomerates from the process were eliminated, finally obtaining 3350 grams of omeprazole pellets, protected by the dibasic amino acid and isolated with a hydroxypropyl methylcellulose coating.

The mixture of excipients made up of hydroxypropyl methylcellulose, polyethylene glycol, polysorbate 80 and titanium dioxide can be replaced, for example, with Opadry White Ys-1-7003 or the like.

Stage III: Hydroalcoholic Enteric Coating of the Particles Obtained in Stage II.

A hydroalcoholic preparation was prepared with A type methacrylic acid copolymer (USP/NF) according to the formula in Table 3 below:

TABLE 3

Composition of the enteric coating suspension.

| Raw Material | Grams/100 g of suspension |
|---|---|
| Ethyl acrylate and methylmethacrylate copolymer | 7.94 |
| Triethyl citrate | 1.59 |
| Titanium Dioxide | 1.00 |
| Isopropyl Alcohol | 84.60 |
| Water | 4.87 |

In the fluid bed a total of 2500 grams of the particles obtained in Stage II were added, after heating the equipment to 35° C., and they were coated with 28775 grams of the above suspension maintaining the temperature between 32 and 38° C. throughout the process. Using a 710 μm mesh agglomerates that could have formed during the process were discarded, finally obtaining omeprazole pellets, protected by the dibasic amino acid, isolated with a coating of hydroxypropyl methylcellulose and gastro-resistant components.

The product revealed good analytical results in a pH 4.5 medium for 45 minutes and the capacity to release said inhibitor at pH 6.8 in no more than 45 minutes according to the assay described in BP 2012 Vol. III.

Stage IV: Drying the Particles with Internal and External Protection Obtained in Stage III and Size Selection.

The particles obtained in Stage III were dried to a humidity level lower than 1% in the same fluid bed equipment. The temperature of the product was maintained at 40° C. throughout the said drying.

Previously and using several samples dried to a different percentage of residual humidity, on an experimental basis it was observed that a humidity content more than 1.0% favoured the breakdown of the omeprazole content in the pellets obtained and simultaneously determined the increase in related substances (or substances originating from the breakdown of omeprazole).

Using a sieving tower (Zonytest) the particles between 420 and 590 microns were selected. The particles sized more than 590 microns were eliminated (approximately 1.5%).

Analytically, it revealed:

1) That the omeprazole content per unit of weight of the pellets obtained was 12.6% and their relative humidity was less than 1%.
2) That the pellets obtained fulfilled the gastro-resistant and dissolution assays described in BP.
3) It showed that in Stage II effective isolation was obtained with a weight gain expressed in hydroxypropyl methylcellulose more than 19%.
4) That the particles fulfilled the assays on related substances described in BP 2012 Vol. III.
5) Accelerated thermal stress assay:
It was shown that the omeprazole pellets obtained and preserved at 60° C. for 10 days did not have a significant reduction of the active ingredient concentration (only 0.70%) and little increase in the value found in related substances (0.50%).
In equal conditions, commercially available pellets with a larger average particle size range used a references presented a reduction in the omeprazole content of about 2.3% and an increase in the related substances of about 3.2%, confirming the advantages of the procedure described.
As the ethyl acrylate and methylmethacrylate copolymer, in a non-limiting manner, it is possible to use: Eudragit L 100.

The procedure described was also applied to esomeprazole.

EXAMPLE II

Preparing Enteric-Coated Pellets that Contain Omeprazole with a Larger Plasticiser Content and Talcum The preparation was carried out in four independent stages that each fulfil specific functions.

Stage I was similar to that described in Example I, but in this case a total of 2000 grams of pure cellulose cores were used and they were coated with 17837 grams of suspension.

Stage II was similar to that described in Example I. With these two stages microparticles of omeprazole were obtained, protected by the dibasic amino acid and isolated with a hydroxypropyl methylcellulose coating. Subsequently with the protected and isolated microparticles enteric-coated pellets were obtained with a greater concentration of plasticiser (triethyl citrate) and talcum to that used in Example I according to the description.

Stage III: Hydroalcoholic Enteric Coating of the Particles Obtained in Stage II.

A hydroalcoholic preparation was prepared with A type methacrylic acid copolymer (USP/NF) according to the following formula:

| Raw Material | Grams/100 g of suspension |
|---|---|
| Methacrylic acid copolymer | 7.94 |
| Triethyl citrate | 2.38 |
| Titanium Dioxide | 1.00 |
| Talcum | 1.00 |
| Isopropyl Alcohol | 83.28 |
| Water | 4.40 |

A total of 1300 grams of the particles obtained in Stage II were added to a fluid bed equipment, previously heated to 35° C., and they were coated with 13930 grams of the suspension above maintaining the temperature between 30 and 35° C. throughout the whole process. Using a 710 µm sieve agglomerates formed in the process were discarded, finally obtaining omeprazole pellets, protected by the dibasic amino acid, isolated with a coating of hydroxypropyl methylcellulose and gastro-resistant components.

The product revealed appropriate stability in the pH 4.5 medium for 45 minutes and the capacity to release said inhibitor at pH 6.8 in no more than 45 minutes according to the assay described in BP 2012 Vol. III.

Stage IV: Drying the Particles with Internal and External Protection Obtained in Stage III and Size Selection.

The particles obtained in Stage III were dried to a humidity level lower than 1% in the same fluid bed equipment. The temperature of the product was maintained at 40° C. throughout the drying.

Using the sieving tower (Zonytest) the particle size distribution was determined. It was observed that 97% of the particles had a size between 420 and 590 microns. The particles with a size over 590 microns were eliminated (approximately 1.5%).

Analytically: The behaviour of the pellets obtained by increasing the plasticiser content to 30% was similar to the pellets obtained according to Example I above with respect to: humidity (lower than 1%) and gastro-resistancy, dissolution and related substances assays. The omeprazole content was 15.0%.

The larger content of triethyl citrate during Stage III determined a more flexible coating resistant to the compression strength during the preparation of oral dispersion tablets according to the general procedure described in subsequent examples.

EXAMPLE III

Preparation of Enteric-Coated Pellets Containing Omeprazole and Pure Cellulose Core with Average Diameter Between 300 And 500 Microns Starting with pure cellulose (100%) neutral cores, sized between 500 and 300 µm and pure omeprazole active ingredient, using successive stages of bottom spray coating using hydroalcoholic suspensions, omeprazole enteric-coated pellets were obtained, sized between 500 and 710 µm.

The preparation was carried out in four independent stages with each one fulfilling specific functions. They were:

Stage I: Coating Cellulose Cores with a Hydroalcoholic Suspension Containing Dissolved Omeprazole, and a Dibasic Amino Acid in Amorphous State, a Suspension that is Formed by Adding Talcum to the Solution of Omeprazole and Amino Acid and Subsequently Adding Polyvinylpyrrolidone as the Agent Inhibiting the Recrystallisation of the Dibasic Amino Acid Present in the Suspension.

As the first step, the suspension was prepared containing the proton pump inhibitor, the dibasic amino acid (1-arginine) as internal protector dissolved in the solvent, a binding agent (polyvinylpyrrolidone K-30) and talcum, according to the formula in Table 1.

TABLE 1

Composition of the active coating suspension.

| Raw Material | Grams/100 g. of suspension |
|---|---|
| Omeprazole | 14.7 |
| Polyvinylpyrrolidone K-30 | 3.6 |
| L-arginine | 1.5 |
| Talcum | 1.5 |
| Ethanol | 70.8 |
| Water | 7.9 |

The coating suspension was prepared by previously dissolving 1-arginine in water.

Subsequently the ethanol was added, and the omeprazole was dissolved; then talcum was added forming a suspension. The suspension was homogeneised for 20 minutes, the polyvinylpyrrolidone K-30 was added and it was homogeneised for 20 minutes more. Finally the suspension was filtered through a 250 µm mesh.

Using bottom spray, a total of 5704 grams of this suspension was applied over 3000 grams of pure cellulose cores sized between 300 and 500 µm, maintaining the temperature of the product at 40° C. throughout the process. At the end of this stage, a 710 µm sieve was used to eliminate agglomerates that could have formed during the process. Finally obtaining 4106 grams of omeprazole pellets protected by the dibasic amino acid.

Stage II: Isolating the Particles Obtained in Stage I.

A hydroalcoholic suspension was prepared with hydroxypropyl methylcellulose (HPMC) and other components indicated in the formula in Table 2, under stirring for one hour.

TABLE 2

Composition of the isolation coating suspension.

| Raw Material | Grams/100 g. of suspension |
|---|---|
| Hydroxypropyl methylcellulose (6 cp) | 3.9 |
| Hydroxypropyl methylcellulose (3 cp) | 3.9 |
| Polyetylene glycol 400 | 0.96 |
| Polysorbate 80 | 0.12 |
| Titanium Dioxide | 3.9 |
| Isopropyl Alcohol | 70 |
| Water | 17 |

A total of 4000 grams of the cores coated in Stage I were added to fluid bed equipment previously heated to 40° C. and they were coated using bottom spraying with 3335 grams of the above isolation suspension. Throughout the process the temperature was maintained at 38 to 42° C. Using a 710 µm mesh agglomerates from the process were eliminated, finally obtaining a total of 4326 grams of omeprazole pellets, protected by the dibasic amino acid and isolated with a coating of hydroxypropyl methylcellulose.

The mixture of excipients made up of hydroxypropyl methylcellulose, polyethylene glycol, polysorbate 80 and titanium dioxide can be replaced, for example, with Opadry White Ys-1-7003 or the like.

Stage III: Enteric Hydroalcoholic Coating of the Particles Obtained in Stage II.

A hydroalcoholic suspension was prepared with A type methacrylic acid copolymer (USP/NF), according to the formula in the following Table 3:

TABLE 3

Composition of the enteric coating suspension.

| Raw Material | Grams/100 g. of suspension |
|---|---|
| Methacrylic acid copolymer | 7.94 |
| Triethyl citrate | 1.27 |
| Talcum | 0.79 |
| Isopropyl Alcohol | 84.86 |
| Water | 5.14 |

A total of 3600 grams of the particles obtained in Stage II were added to fluid bed equipment, previously heated to 35° C., and they were coated with 21600 grams of the above suspension maintaining the temperature between 32 and 38° C. throughout the process. Using a 1000 µm sieve agglomerates formed during the process were discarded, finally obtaining omeprazole pellets, protected by the dibasic amino acid, isolated with a coating of hydroxypropyl methylcellulose and gastro-resistant components.

The product revealed good results in the pH 4.5 medium for 45 minutes and the capacity to release said inhibitor at pH 6.8 in no more than 45 minutes according to the assay described in BP 2012 Vol. III.

Stage IV: Drying the Particles with Internal and External Protection Obtained in Stage III and Size Selection.

The particles obtained in Stage III were dried to humidity lower than 1% in the same fluid bed equipment, using a temperature of 40° C.

Using a sieving tower (Zonytest) the particle size distribution was determined. It was observed that 93% of the particles were sized between 500 and 710 microns. The larger size particles were eliminated.

Analytically, it was revealed:

1) That the omeprazole content per unit of weight of the pellets obtained was 10.67% and its relative humidity was lower than 1%.

2) Taking a sample prior to drying to humidity lower than said 1%, it was shown unexpectedly that, when the humidity content is more than 1% it quickly accelerates the breakdown of the omeprazole contained in the pellets obtained. Also the presence of related substances is significantly increased.

3) The pellets obtained fulfilled the gastro-resistancy and dissolution assays described in British Pharmacopea.

It was shown that in Stage II effective isolation was obtained with a weight gain expressed in hydroxypropyl methylcellulose greater than 6%.

4) That the particles fulfilled assays on related substances described in BP 2012 Vol. III.

5) Accelerated thermal stress assay:

The reduction in the titration value of the omeprazole pellets with humidity lower than 1% obtained and preserved at 60° C. for 17 days was 1.32% and the increase in the related substances was 1.32%.

In equal conditions, in a period of just 10 days, commercially available pellets with a greater average particle size range used as references showed a reduction in the omeprazole content of about 2.3% and an increase in the related substances of about 3.2%, confirming the advantages of the procedure described.

The difference in behaviour regarding the temperature and time revealed the greater stability of the new pellets in comparison with conventional pellets.

6) Accelerated stability assay:

It was shown that the omeprazole pellets obtained and preserved at 40° C. with 75% RH, for 7 months, did not have any significant reduction in the concentration of the active ingredient and little increase in the value found with related substances.

EXAMPLE IV

Preparation of Enteric-Coated Pellets Containing Omeprazole on Pure Cellulose Core and with Aqueous Enteric Coating Enteric-coated omeprazole pellets were obtained starting with pure cellulose (100%) neutral cores with an average size between 150 and 300 microns, coating them with successive steps of bottom spraying.

Omeprazole microparticles previously protected by a dibasic amino acid and isolated with a hydroxypropyl methylcellulose coating were coated with an aqueous enteric coating, obtaining pellets sized between 350 and 500 μm and with an omeprazole content over 20%.

The preparation was made in four independent stages each one fulfilling specific functions. These were:

Stage I: Coating Cellulose Cores with a Hydroalcoholic Suspension Containing Omeprazole and a Dibasic Amino Acid Dissolved in an Ethanol-Water Mixture (90/10) the Suspension Being Formed by Adding Talcum and to the Suspension Formed the Agent Inhibiting the Recrystallisation of the Dibasic Amino Acid (Polyvinylpyrrolidone) and Homogeneisation is Added It was carried out according to Stage I of Example I with the same formula and process conditions.

A total of 17837 grams of hydroalcoholic suspension of omeprazole were applied over 2000 grams of pure cellulose cores.

Stage II: Isolation of the Particles Obtained in Stage I.

It was carried out with the same formula, preparation and process conditions used in Stage II of Example I.

Stage III: Aqueous Enteric Coating of the Particles Obtained in Stage II.

An aqueous suspension of C Type methacrylic acid copolymer (USP/NF) was prepared according to the formula in Table 1:

TABLE 1 composition of the enteric coating suspension.

| Raw Material | Grams/100 g. of suspension |
|---|---|
| Methacrylic acid and ethyl methacrylate copolymer | 12.6 |
| Triethyl citrate | 2.52 |
| Glyceryl monostearate | 0.95 |
| Polysorbate 80 | 0.13 |
| Water | 83.8 |

A total of 1300 grams of the particles obtained in Stage II were added to the fluid bed equipment, previously heated to 35° C., and they were coated with 4336 grams of the above suspension maintaining the temperature between 25 and 28° C. throughout the process. Using a 590 μm sieve the agglomerates formed in the process were discarded, finally obtaining omeprazole pellets, protected by the dibasic amino acid, isolated with a layer of methylcellulose and gastro-resistant components.

The product revealed good analytical results in a pH 4.5 medium for 45 minutes and the capacity to release said inhibitor at pH 6.8 in no more than 45 minutes according to the assay described in BP 2012 Vol. III.

Stage IV: Drying the Particles with Internal and External Protection Obtained in Stage III and Size Selection.

The particles obtained in Stage III were dried to humidity lower than 1% in the same fluid bed equipment, using a temperature of 40° C.

Using a sieving tower (Zonytest) the particle size distribution was determined. It was observed that 92% of the particles were sized between 350 and 500 microns. The particles sized over 590 microns (aporoximately 5%) were eliminated.

Analytically, it showed:

1) That the omeprazole content per unit of weight of the pellets with relative humidity below 1% obtained, was 23.4%.

2) Taking a sample before drying, it was shown that when the humidity content is over 1% the breakdown speed of the omeprazole contained in the pellets is accelerated vis-à-vis the temperature and the existence of related substances increases.

3) That the pellets obtained fulfilled the gastro-resistancy and dissolution assays described in BP 2012 Vol. III.

It was shown that in Stage II effective isolation was obtained with a weight gain expressed in hydroxypropyl methylcellulose over 19%.

4) That the particles fulfilled the related substance assays described in USP 32, page 3426.

5) Accelerated thermal stress assay:

It was revealed that the omeprazole pellets with humidity below 1% obtained and preserved at 60° C. for 10 days do not have a significant reduction in titration value and little increase in the value found with related substances (0.6%).

In equal conditions commercially available pellets with an average particle size range used as references revealed a reduction in the omeprazole content of about 2.3% and an increase in the related substances of about 3.2%, confirming the advantages of the procedure described.

As the methacrylic acid and ethyl methacrylate copolymer, Eudragit L30 D55 can be used.

Pellets were obtained with humidity below 1% and an omeprazole content between 20 and 24%.

EXAMPLE V

Preparing Enteric-Coated Pellets Containing Omeprazole on Pure Cellulose Core and Aqueous Enteric Coating (Alternative Procedure to Example IV with the Addition of Talcum and Titanium Dioxide)

Starting with pure cellulose (100%) neutral cores with an average size between 150 and 300 microns and with successive stages of bottom spray coating, omeprazole enteric-coated pellets were obtained.

Microparticles of omeprazole previously protected by a dibasic amino acid and isolated with a cover of hydroxypropyl methylcellulose were coated with an aqueous enteric coating suspension, obtaining pellets sized between 350 and 500 μm and with a high omeprazole content.

The preparation was carried out in four independent stages each one fulfilling specific functions. They were:

Stage I: Coating Cellulose Cores with a Hydroalcoholic Suspension Containing Dissolved Omeprazole and a Dibasic Amino Acid in an Ethanol-Water Mixture (90/10); the Suspension Being Formed by Adding Talcum and Subsequently the Agent Inhibiting the Recrystallisation (Polyvinylpyrrolidone) of the Dibasic Amino Acid and Homogenisation, is Added.

Stage I was carried out according to Example I with the same formula and process conditions.

Stage II: Isolating the Particles Obtained in Stage I.

It was carried out with the same formula, preparation and process conditions used in Stage II of Example I.

Stage III: Aqueous Enteric Coating of the Particles Obtained in Stage II.

An aqueous suspension of C Type methacrylic acid copolymer (USP/NF) was prepared according to

TABLE 1

The formula in Table 1: composition of the enteric coating suspension.

| Raw material | Grams/100 g. de suspension |
| --- | --- |
| Methacrylic acid and ethyly methacrylate copolymer | 11.7 |
| Triethyl citrate | 2.0 |
| Glyceryl monostearate | 0.7 |
| Polysorbate 80 | 0.1 |
| Talcum | 0.6 |
| Titanium dioxide | 0.6 |
| Water | 84.1 |

A total of 5650 grams of the particles obtained in Stage II were added to a fluid bed and 22658 grams of suspension were added, previously heating the equipment to 35 degrees, finally obtaining omeprazole pellets, protected by the dibasic amino acid, isolated with a cover of hydroxypropyl methylcellulose and gastro-resistant products.

The product revealed good results in a pH 4.5 medium for 45 minutes and the capacity to release said inhibitor at pH 6.8 in no more than 45 minutes according to the assay described in BP 2012 Vol. III.

Stage IV: Drying the Particles with Internal and External Protection Obtained in Stage III and Size Selection.

The particles obtained in Stage III were dried to humidity lower than 1% in the same fluid bed equipment, using a temperature of 40° C.

Using a sieving tower (Zonytest) the particle size distribution was determined. It was observed that 92% of the particles were sized between 350 and 500 microns. The particles sized over 590 microns (approximately 5%) were eliminated.

Analyticall, it was revealed:

1) That the omeprazole content per unit of weight of the pellets obtained was 20.4% and their relative humidity was lower than 0.7%.

2) That a humidity content over 1% accelerates breakdown of the omeprazole contained in the pellets obtained and increases the existence of related substances.

3) That the pellets obtained fulfilled the gastro-resistancy and dissolution assays described in BP 2012 Vol. III.

It was revealed that in Stage II effective isolation is obtained with a weight gain expressed in hydroxypropyl methylcellulose over 19%.

4) That the particles fulfilled related substance assays described in USP 32, page 3426. and BP 2012 Vol. III.

With the procedure described above pellets were obtained with humidity lower than 1% and an omeprazole content between 20.0% and 24.0%.

EXAMPLE VI

Preparing Oral Dispersion Tablets (ODT) Using Pellets Containing Omeprazole Over Pure Cellulose Cores and with Aqueous Enteric Coating in a Sufficient Amount for a 20 mg Dosage Starting with the omeprazole enteric-coated pellets described in Example IV, oral dispersion tablets were obtained by direct compression. The formula is made up of approximately 30% of omeprazole pellets and 70% of excipients for direct compression usually used in pharmacy. The following compositions were prepared:

TABLE 1

Composition of the oral dispersion tablets,

| Raw material | Formula A % of each component | Formula B % of each component |
| --- | --- | --- |
| Omeprazole pellets (sufficient amount for a 20 mg/unit dosage) | 28.5 | 30.2 |
| Pharmaburst 500 (*) | 60.3 | 43.8 |
| Crosslinked Povidone | 3.0 | 5.0 |
| Colloidal anhydrous silicon | 0.5 | 0.5 |
| Citric Acid | 3.0 | 3.0 |
| Lime-Lemon Essence | 2.0 | 0 |
| Peppermint essence | 0 | 4.0 |
| Sucralose | 1.7 | 2.5 |
| Microcrystalline cellulose | 0 | 10.0 |
| Sodium Stearyl Fumarate | 1.0 | 1.0 |

(*) Pharmaburst: coprocessed product made up of mannitol, sorbitol, maltitol, crospovidone, copovidone and silicon dioxide.

The preparation was carried out in three independent stages. These were:

Stage I: Mixing the Omeprazole Pellets and the Excipients.

All the excipients, except the lubricant (sodium stearyl fumarate), were sieved with a 25 mesh sieve, to remove agglomerates. Then they were added to a suitably sized conical mixer, together with the omeprazole pellets and mixed for 20 minutes at 80 rpm.

Stage II: Lubricating the Mixture.

The sodium stearyl fumarate was first passed through a 35 mesh sieve, it was added to the mixer containing the mixture obtained in Stage I and mixed for 5 minutes at 80 rpm.

Stage III: Compressing the Final Mixture.

To compress the mixture a Piccola compressor was used with 4 punches. Samples were obtained in 2 different formats, round with a 9 mm diameter and square with 10 mm sides. Compression strengths of 5.5 KN, 7.5 KN and 10.5 KN were used for the round format and 6.1 KN, 9.1 KN and 13.0 KN for the square format. All at a unit weight of 350 mg. The mixture revealed good flow and compactability throughout the process in all cases.

Controls Applied to Each Simple Obtained:

The samples obtained in Stage III with different compression strengths were subjected to the following controls:

1) Control of weight uniformity, hardness, thickness and diameter.

2) Friability test (acc. to USP 32).

3) Disintegration control.

All the samples showed a variation in individual weight less than 5.0% and less than 2.5% in the average weight. For formula A in round format, the average hardnesses of each sample were 2.7 SC, 6.7 SC and 10.8 SC for the strengths of 5.5 KN 7.5 KN and 10.5 KN respectively. The tablet thicknesses were 4.2 mm, 3.9 mm and 3.8 mm with respect to the samples obtained with an increasing compression strength. For formula B in square format, the average hardnesses of each sample were 3.3 SC, 5.6 SC and 7.0 SC for the strengths of 6.1 KN, 9.1 KN and 13.0 KN respectively. The tablet thicknesses were 4.9 mm, 4.8 mm and 4.6 mm with respect to the samples obtained with an increasing compression strength.

In the first case, the samples obtained at 7.5 KN and 10.5 KN had friability values below 0.5% and a good appearance at the end of the test. However, the sample of tablets obtained at 5.5 Kn had friability values greater than 0.5% and therefore, they were discarded. For the square format and formula B, all the samples obtained had friability values less than 0.5% and a good appearance.

The disintegration time in water, for formula A and the round format, was 6 seconds for the 5.5 KN strength, 12 seconds for the 7.5 KN strength and 20 seconds for the 10.5 KN strength. For formula B and the square format, the times of 12 seconds, 18 seconds and 20 seconds were obtained with an increasing compression strength.

Analytical Controls

The controls carried out were: assessment of the omeprazole content, uniformity of the unit dose, gastro-resistancy and dissolution tests described in BP 2012 Vol. III.

In this example it was shown that starting with the microparticles obtained in Example IV (omeprazole microparticles, protected by a dibasic amino acid, isolated with a layer of hydroxypropyl methylcellulose and coated with an aqueous enteric coating suspension, with a final size between 350 and 500 μm) it is possible to obtain oral dispersion tablets.

The procedure described allows for preparing oral dispersion tablets for the dosages of 10 and 40 mg of omeprazole compressed at a unit weight of 175 mg and 700 mg respectively.

With procedures similar to this one, oral dispersion tablets were obtained starting with:

a) Omeprazole microparticles, protected by a dibasic amino acid, isolated with a layer of hydroxypropyl methylcellulose and coated with an enteric coating of hydroalcoholic suspension, with a final size between 500 and 710 μm (described in Example III).

b) Omeprazole microparticles, protected by a dibasic amino acid, isolated with a layer of hydroxypropyl methylcellulose and coated with an enteric coating of hydroalcoholic suspension, with a final size between 420 and 590 μm (described in Example I and II).

In all cases the disintegration time in the buccal cavity was less than 30 seconds and preferably less than 15 seconds.

In a similar way oral dispersion tablets were prepared, containing indistinctively: esomeprazole and omeprazole with 10 or 40 mg.

EXAMPLE VII

Preparing Capsules with Enteric Omeprazole Microparticles in a Sufficient Amount for a 20 mg Dosage of Active Ingredient Starting with the enteric omeprazole pellets described in the examples above, a sufficient amount of microparticles was metered into rigid gelatine capsules to obtain a 20 mg dose of pure omeprazole active ingredient per capsule.

When Choosing the Size of the Capsule, the Following was Considered:

a) that the new size of the enteric-coated pellets obtained is significantly smaller than the commercially available enteric-coated pellets that have an average diameter of 1000 microns or more.

b) That the omeprazole content in the enteric-coated pellets according to the various examples above was greater than that in the commercially available enteric-coated pellets.

Specifically the pellets obtained in the corresponding examples showed:

| Example | Cellulose cores (diameter (microns)) | Enteric coating (Stage III) (medium) | OMEPRAZOLE | Pellets AVERAGE SIZE microns |
|---|---|---|---|---|
| I | 150/300 | Hydroalcoholic | 12.6% | 420/590 |
| II | 150/300 | Hydroalcoholic | 15.0% | 420/590 |
| III | 300/500 | Hydroalcoholic | 10.6% | 500/710 |
| IV | 150/300 | Aqueous | 23.4% | 350/500 |
| V | 150/300 | Aqueous | 20.4% | 350/500 | c) the pellets with a content higher than 10.5% were chosen, and preferably the pellets with a content higher than 12.0% by weight.

d) 20 mg. omeprazole expressed in active ingredient showed that they can be added to smaller size capsules than those usually used (No. 2) and commercially available.

Procedure:

The microparticles obtained were metered into rigid conisnap gelatine capsules, white and yellow in colour. A Zuma Brand encapsulating machine was used with manual filling.

A total of 200 capsules were made with the enteric-coated pellets from each of the examples mentioned.

With the enteric-coated pellets prepared according to Examples IV and V, empty capsules as small as possible and industrially available were filled. Particularly, capsules No. 5.

In all cases the capsules containing 20 mg of omeprazole in the form of pellets according to this invention were smaller than the commercial available capsules with 20 mg omeprazole.

The following checks were made on the prepared capsules:
Filling uniformity (using average weight), variation less than 2.5%.
Individual weight, with variation less than 5%.
Average weight: 98.04 mg (95.59-100.49).
Individual weight: 98.04 mg (93.14-102.94).
Comparison with Capsules of Commercial Products with Equal Content:
Using commercial products as a reference and particularly, those called Ulcozol 20 mg. (by Laboratorios Bagó S.A.) and Buscasan 24 (by Laboratorios Boheringer Ingelheim) which also contain 20 mg. of omeprazole in the form of enteric-coated pellets, it was observed that they are placed inside capsule No. 2 that is bigger than the capsules obtained in this example (capsules No. 5).
The Smaller Size of the Capsules (No. 5, 4 ó 3) that can be Prepared with the New Enteric-Coated Pellets According to this Invention Determine the Following Practical Advantages:
1) Less input and cost during the primary packaging of the capsules in aluminium-aluminium blisters. Significant industrial advantage.
2) More easily swallowed by patients.
20 volunteers received normal size commercial capsules with 20 mg of omeprazole and also smaller size capsules containing 20 mg. of omeprazole according to this example. They all preferred the smaller capsules.
3) In 20 healthy volunteers another possibility of use was revealed. That is, opening the capsule and pouring its content into liquids or foods and then swallowing them. The small size of the enteric-coated pellets did not cause discomfort when administered.
Both alternatives (swallowing complete small size capsules or the powder from the capsules) revealed their practicality in patients and particularly, patients with swallowing difficulties.
Capsules containing 10 and 40 mg of omeprazole were also filled.
The characteristics mentioned are a direct consequence of the small size and high content of the omeprazole pure active ingredient contained in the enteric-coated pellets prepared according to the examples described above.

EXAMPLE VIII

Preparing Powder for Oral Suspension that Contains Omeprazole Pellets, Prepared Over Pure Cellulose Cores and with an Aqueous Enteric Coating Starting with the enteric-coated omeprazole pellets described in Example 4 sized between 350 and 500 microns and with an omeprazole content over 20.0%, a powder mixture for oral suspension was obtained, which was metered into sachets, with a sufficient quantity for a dose corresponding to 20 mg of omeprazole pure active ingredient.
The formula is made up of approximately from 2% to 3% of omeprazole pellets, 20% of a viscous agent that provides stability to the suspension, 4% of citric acid which gives slight acidity to the suspension protecting the enteric nature of the pellets, 70% of sugar and flavourings commonly used in pharmacy. The following formulae were prepared:

TABLE 1

Composition of the power mixture for oral suspension

| Raw material | Formula A % of each component | Formula B % of each component |
|---|---|---|
| Omeprazole pellets (sufficient amount for a 20 mg/unit dose) | 3.3% | 2.1% |
| Sucralose | 0.8% | 0.8% |
| Lemon essence | | 0.7% |
| Orange essence | 0.7% | 0% |
| Cream essence | 0.7% | 0% |
| Masking flavor | 0 | 0.7% |
| Citric acid | 4.0% | 4.0% |
| Microcrystalline celluose and Sodium carboxymethyl cellulose | 20.0% | 20.1% |
| Sugar | 70.5% | 71.8% |

The preparation was carried out in two independent Stages. These were:
Stage I: Mixing the Excipients.
All the excipients, except the sugar, were sieved using a 25 mesh sieve, to remove the agglomerates therefrom. Then they were added to a suitably sized conical mixer, together with the corresponding amount of sugar and mixed for 15 minutes at 80 rpm.
Stage II: Metering.
Metering was carried out using a sachet filling machine with two feeding stations. The mixture of excipients was metered in the first station, and the enteric-coated omeprazole pellets in the second. The supply to each station was calibrated beforehand, each independently from the other, so that the amount of pellets metered per sachet was the sufficient amount for a 20 mg dose of omeprazole, and the amount of excipients metered in the first station was the sufficient amount to obtain a final content of 5 grams per sachet.
The material of the sachet used was a suitable aluminium sheet that enables protecting the product from light and ambient humidity.
Controls Carried Out on Each Sample Obtained:
The samples obtained in Stage II were subjected to the following controls:
1) Control of weight uniformity. By emptying the contents of each metered dose only with the enteric-coated omeprazole pellets.
2) Control of weight uniformity. By emptying the contents of each dose only with the excipient mixture.
3) Control of weight uniformity. By emptying the content of each final unit.
4) Airtightness control
5) Visual appearance control.
All the samples had an individual weight variation lower than 5.0% and lower than 2.5% in the average weight.
Analytical Controls
The controls carried out were: assessment of the omeprazole content, uniformity of unit dose, gastro-resistance and dissolution assays described in BP 2012 Vol. III.
The Following were Prepared with the Same Formulas Described Previously and Modifying the Metering Per Unit in a Proportional Way:
a) powder for suspension in sachets containing 10 and 40 mg of omeprazole per dose unit, at a final weight of 2.5 g and 10 g respectively.

b) powder for suspension packaged in single and multiple dose vials that provide per dose unit 10, 20 or 40 mg. of omeprazole respectively.

Swallowing the powder reconstituted with water, originating from sachets or vials and with a different omeprazole content, at no time caused swallowing problems among the volunteers who took the respective suspensions thanks to the size of the pellets containing said powder.

In all cases, the reconstituted powder was well accepted.

EXAMPLE IX

Sugar-Free Powder for Suspension

It was prepared according to Example VIII above, with the omeprazole pellets with a pure cellulose (100%) core and following Stages I and II described above, but eliminating the sugar mentioned in Table 1 above, and increasing up to 5.0% the percentage of sucralose quoted in said Table.

The sucralose added as a sweetener is practically not absorbed, and it does not alter the blood glucose levels, as is known and described in the bibliography.

The sucralose's behaviour, together with the pure cellulose cores free of described sugars, determines that the preparation in powder form for suspension is particularly beneficial for patients with diabetes

EXAMPLE X

Pharmaceutical Composition Containing Omeprazole Pellets in Association with Microcapsules of Sodium Diclofenac The enteric-coated pellets prepared as described in Example IV and sized between 350 and 500 microns and with a high omeprazole content were associated with enteric-coated sodium diclofenac microcapsules.

The diclofenac microcapsules were prepared previously as described in the international patent application published under number WO 2013/139377 A1 by the same applications as this invention.

The prepared associations contain 25 to 100 mg of microencapsulated and enteric-coated sodium diclofenac and between 10 and 40 mg of omeprazole pellets.

The following were prepared:

a) Oral disintegration tablets (ODT) according to the procedure described in Example IV.

b) Capsules, according to the procedure described in Example VII. In this case the chosen capsules were size 4.

c) Powder for oral suspension, according to Example VIII.

In all cases, the preparation was carried out with the same excipients and procedures mentioned in each example. To the mixtures described in each example the diclofenac microcapsules were added in an amount between 25 and 100 mg of sodium diclofenac, previously corrected by titration value.

The compositions obtained had a greater weight than those mentioned for each composition in Examples IV, VII and VIII but there physical characteristics were similar.

The invention claimed is:

1. A method for preparing enteric-coated pellets containing a proton pump inhibitor with benzimidazole structure, comprising:

I) coating pure cellulose cores, wherein the cores have a particle size range: between 150 and 500 microns, with a hydroalcoholic suspension that contains each of the proton pump inhibitor, a dibasic amino acid lysine, histidine and L-arginine, and polyvinylpyrrolidone, thereby obtaining coated cellulose cores;

II) isolating the coated cellulose cores to obtain isolated particles;

III) applying an enteric coating to the isolated particles to obtain enteric-coated particles; and IV) drying the enteric-coated particles and separating the enteric-coated particles by size, thereby obtaining enteric-coated pellets, wherein the dibasic amino acid exists in an amount less than or equal to 10% by weight relation to the weight of the proton pump inhibitor; and pure cellulose cores with an average diameter between 150 and 300 microns result in enteric-coated pellets that have an average diameter between 350 and 590 microns, and pure cellulose cores with an average diameter between 300 and 500 microns result in enteric-coated pellets that have an average diameter between 500 and 710 microns.

2. The method according to claim 1, further comprising preparing the hydroalcoholic suspension by:

dissolving the dibasic amino acid in water to obtain an aqueous solution;

adding ethanol to the aqueous solution to obtain a hydroalcoholic solution having an ethanol-water ratio between 80:20 and 95:5; and adding the proton pump inhibitor to the hydroalcoholic solution as far as complete dissolution of the proton pump to obtain a hydroalcoholic solution comprising the proton pump inhibitor;

adding talcum to the hydroalcoholic solution comprising the proton pump inhibitor to form a suspension;

adding polyvinylpyrrolidone to the suspension under stirring between 8500 and 10500 r.p.m;

filtering the suspension to obtain a filtered suspension; and maintaining the filtered suspension under stirring, thereby obtaining the hydroalcoholic suspension.

3. The method according to claim 1, wherein the enteric-coated pellets have a proton pump inhibitor content greater than 10.5% by weight with respect to the total weight of the pellets.

4. The method according to claim 2, wherein the amount of polyvinylpyrrolidone added to the solution is sufficient to inhibit crystallization of the dibasic amino acid and the amount of polyvinylpyrrolidone added to the solution is less than or equal to 4% by weight of the solution.

5. The method according to claim 1, wherein:

isolating the coated cellulose cores comprises contacting the coated cellulose cores with an isolating suspension;

the isolating suspension comprises, by weight, from 5% to 7.2% hydroxypropyl methylcellulose, from 0.5 to 1% polyethylene glycol 400, from 0.1 to 0.14% polysorbate 80, from 2.5 to 3.6% titanium dioxide, from 15.0 to 17% water and from 76.9 to 71% isopropanol; and the coated cellulose cores are contacted with the isolating suspension in a fluid bed at a temperature of 38 to 45° C.

6. The method according to claim 1, wherein:

the enteric coating comprises, by weight, 6% to 8% methacrylic acid and methyl methacrylate copolymer, from 1.5% to 2.50% triethyl citrate and up to 1% of titanium dioxide in a mixture of isopropyl alcohol and water in a proportion between 90:10 and 95:5; and the enteric coating is applied to the isolated particles in a fluid bed at a temperature between 30 and 38° C.

7. The method according to claim 1, wherein:
the enteric coating is an aqueous suspension comprising, by weight, 11% to 13% methacrylic acid and ethyl methacrylate copolymer, up to 3% triethyl citrate, up to 1% glyceryl monostearate, up to 0.2% polysorbate 80 and up to 1.0% titanium dioxide in water; and
the enteric coating is applied to the isolated particles in a fluid bed while maintaining the temperature of the fluid bed between 25 and 35° C. throughout the application process.

8. The method according to claim 1, wherein the enteric-coated particles are dried to a humidity lower than 1% at 40° C.

9. The method according to claim 1, wherein the pure cellulose cores have a particle size range between 150 and 300 microns.

10. The method according to claim 9, wherein enteric-coated pellets are obtained sized between 350 and 590 microns and only between 5% and 7% of the enteric-coated pellets have a diameter greater than 500 microns.

11. The method according to claim 1, wherein the proton pump inhibitor is omeprazole or esomeprazole.

* * * * *